United States Patent [19]
Mortazavi et al.

[11] Patent Number: 6,044,294
[45] Date of Patent: Mar. 28, 2000

[54] METHODS AND APPARATUS FOR MEASURING IMPEDANCE IN THE BODY

[75] Inventors: Said Mortazavi, Sherman Oaks; Euljoon Park, Stevenson Ranch; Gene A. Bornzin, Simi Valley; Joseph J. Florio, La Canada, all of Calif.; Jason A. Sholder, Towaco, N.J.; Robert R. Weyant, Durham, Oreg.

[73] Assignee: Pacesetter, Inc., Sylmar, Calif.

[21] Appl. No.: 08/766,636

[22] Filed: Dec. 13, 1996

Related U.S. Application Data

[60] Provisional application No. 60/011,583, Dec. 15, 1995.

[51] Int. Cl.[7] ........................................... A61B 5/05
[52] U.S. Cl. .................................. 600/547; 607/9
[58] Field of Search ..................... 600/547, 373, 600/374, 377; 607/5, 7, 8, 9, 11, 14, 15, 17, 27, 28, 32

[56] References Cited

U.S. PATENT DOCUMENTS

| | | | |
|---|---|---|---|
| 3,924,606 | 12/1975 | Silva et al. ................... | 600/547 |
| 4,702,253 | 10/1987 | Nappholz et al. . | |
| 4,733,667 | 3/1988 | Olive et al. ................... | 607/24 |
| 4,773,401 | 9/1988 | Citak et al. ................... | 607/17 |
| 4,901,725 | 2/1990 | Nappholz et al. ........... | 607/17 |
| 5,137,019 | 8/1992 | Pederson et al. ............ | 607/20 |
| 5,154,171 | 10/1992 | Chirife ......................... | 607/24 |
| 5,179,946 | 1/1993 | Weiss ........................... | 607/4 |
| 5,235,976 | 8/1993 | Spinelli ....................... | 607/25 |
| 5,318,596 | 6/1994 | Barreras et al. ............. | 607/19 |
| 5,361,776 | 11/1994 | Samuelson et al. ......... | 607/9 |
| 5,417,717 | 5/1995 | Salo et al. ................... | 607/18 |
| 5,534,018 | 7/1996 | Wahlstrand et al. ........ | 607/27 |
| 5,683,431 | 11/1997 | Wang .......................... | 607/28 |
| 5,738,105 | 4/1998 | Kroll ........................... | 600/510 |
| 5,749,369 | 5/1998 | Rabinovich et al. ........ | 600/547 |

OTHER PUBLICATIONS

Alt, Eckhard, et al., "Initial Clinical Experience with a New Dual Sensor SSIR Pacemaker Controlled by Body Activity and Minute Ventilation," *PACE*, vol. 18, pp. 1487–1495 (Aug. 1995).

*Telectronics Meta MV 1202 Physician's Manual*, (Telectronics, Inc., undated).

*Primary Examiner*—Richard J. Apley
*Assistant Examiner*—Justine R. Yu

[57] ABSTRACT

Methods and apparatus are provided for measuring the impedance of a patient's body. Pulse generating circuitry within a rate-responsive pacemaker is used to generate an impedance measurement signal that is applied to the body of the patient with conventional pacemaker leads. The impedance measurement signal contains a series of multiphasic impedance measurement waveforms, which have no net DC value and zero value after second integration. The impedance measurement signal allows the impedance of the body to be measured without interfering with external cardiac monitoring equipment such as electrocardiogram machines.

22 Claims, 7 Drawing Sheets

METHODS AND APPARATUS FOR MEASURING IMPEDANCE IN THE BODY

This application claims the benefit of U.S. Provisional Application No. 06/011,583, filed Dec. 15, 1995.

BACKGROUND OF THE INVENTION

This invention relates to methods and apparatus for measuring the impedance of a patient's body, and more particularly, to techniques for measuring body impedance for use by a rate-responsive pacemaker.

Pacemakers are used to treat a variety of cardiac conditions. Some pacemakers simply provide pacing pulses to a patient's heart at a fixed rate. More sophisticated devices contain sensing circuitry that allows the pacemaker to monitor a patient's heartbeat signals. For example, some pacemakers can monitor a patient's atrial heartbeat signals and provide corresponding ventricular pacing pulses, which allows the patient's cardiac output to be adjusted depending on the patient's intrinsic atrial heart rate.

However, in many situations there is no reliable normal heart rhythm that can be monitored by a pacemaker. Because the cardiac need of a patient varies depending on the patient's physical activity level, rate-responsive pacemakers have been developed that provide pacing pulses at a rate based on the patient's need for cardiac output. Some rate-responsive pacemakers contain accelerometer-based activity sensors, which assess a patient's level of physical activity by measuring the patient's body movements. When the measured frequency and intensity of a patient's movements are high, the patient's heart is paced at a correspondingly high rate. Although this approach is generally satisfactory, many rate-responsive pacemakers that use activity sensors are unable to clearly differentiate between body movements due to physical activity and body movements due to external sources (e.g., body movements experienced during an automobile ride).

Other rate-responsive pacemakers use oxygen sensors to measure a patient's blood-oxygen level. Rate-responsive pacemakers that use oxygen sensors adjust the pacing rate to maintain a suitable oxygen level. However, oxygen sensors require the use of a special pacemaker lead.

Another approach that has been used to assess a patient's need for cardiac output is to attempt to determine the amount of air being inhaled by the patient. Taking breaths deeply and frequently indicates that there is a high need for cardiac output. When a patient inhales, the pressure in the chest cavity drops, which causes the impedance of the chest cavity to drop. Measuring the impedance of the chest cavity has been found to provide a good indication of the amount of air being inhaled by a patient. An advantage of monitoring the impedance of the chest cavity to assess cardiac need is that the pacemaker is unaffected by body movements due to external sources and does not require the use of special leads.

One way for the pacemaker to measure body impedance is to apply a current signal of a known magnitude and waveform across the patient's chest. The resulting voltage signal across the body can be measured by sensing circuitry. The impedance is calculated based on the known magnitude of the applied current signal and the measured magnitude of the voltage signal.

Although signals with low frequency content are suitable for measuring body impedance, they often interfere with measurements made using external equipment such as electrocardiogram (ECG) machines, which are sensitive to signals in the 1 Hz to 240 Hz range. Interference from the signal used for impedance measurements is undesirable, because it makes reading the ECG signal difficult.

What is needed therefore is a technique for measuring body impedance without interfering with external cardiac monitoring equipment such as ECG machines.

SUMMARY OF THE INVENTION

In accordance with the principles of the present invention, a rate-responsive pacemaker is provided that measures the impedance of a patient's body. The pacemaker uses the impedance measurements to determine the rate at which to pace a patient's heart. The pacemaker has control circuitry to direct the operation of the pacemaker. Input circuitry connected to the control circuitry is used to monitor the patient's heartbeat signal. Output circuitry provides pacing pulses to the heart.

The output circuitry also generates an impedance measurement signal that is applied to the patient's body. Preferably, the output circuitry contains current source circuitry for generating an impedance measurement current signal. Applying the impedance measurement current signal across the patient's body results in a voltage that is measured by voltage measurement circuitry within the input circuitry. The pacemaker determines the rate at which to apply pacing pulses to the patient's heart by analyzing the magnitudes of the impedance measurement current signal and the corresponding voltage signal. The impedance measurement signal that is generated by the output circuitry preferably is made up of a series of multiphasic waveforms, each with a duration of approximately 152.5 $\mu$s.

BRIEF DESCRIPTION OF THE DRAWINGS

The above and other advantages of the invention will be apparent upon consideration of the following detailed description, taken in conjunction with the accompanying drawings, in which like reference numerals refer to like parts throughout, and in which.

DETAILED DESCRIPTION OF THE PREFERRED EMBODIMENTS

Figure 1:
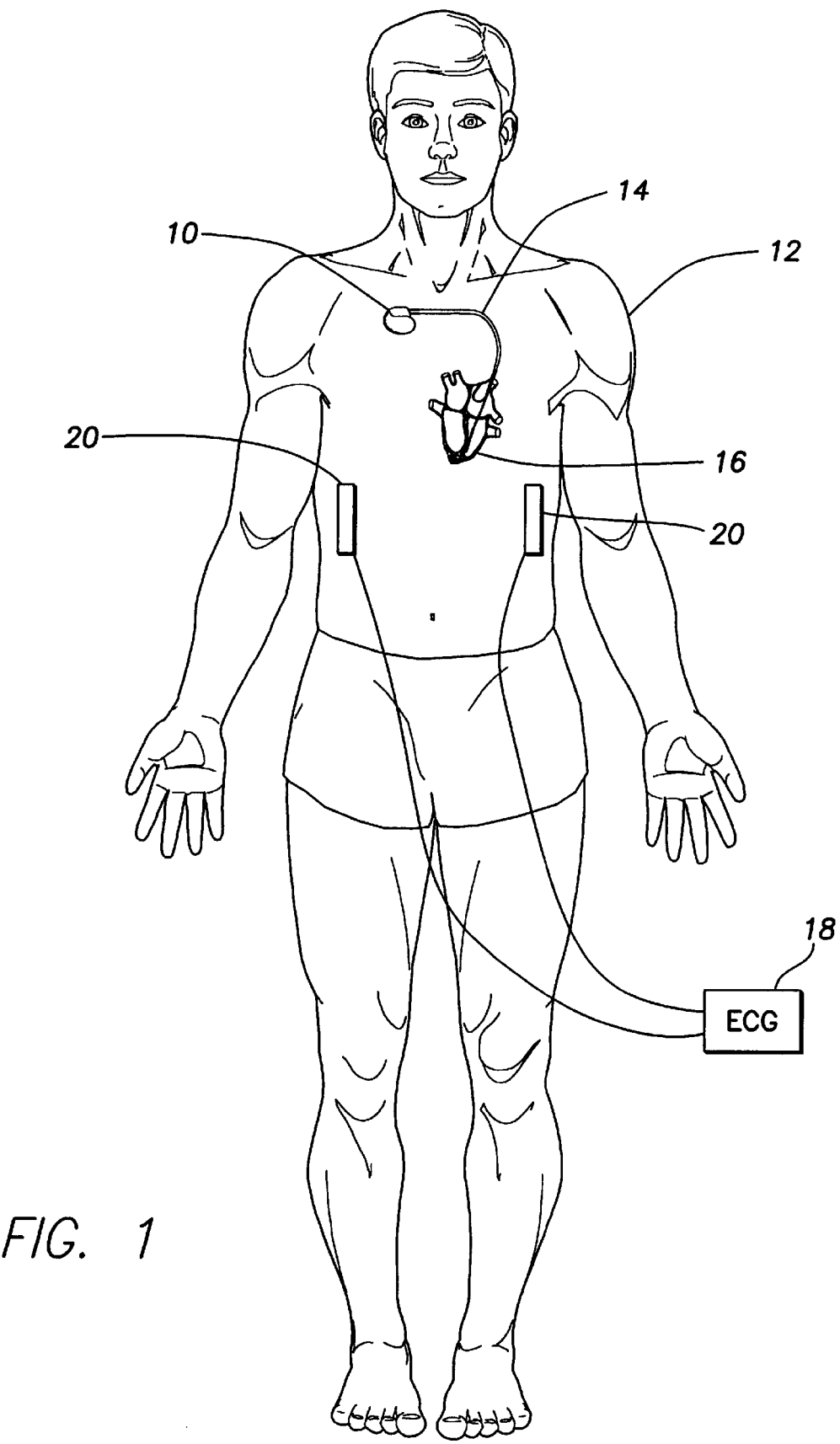
FIG. 1 is a perspective view of a patient showing typical connections made by an electrocardiogram machine and a pacemaker in accordance with the present invention.

A pacemaker 10 is shown implanted in a patient 12 in FIG. 1. The pacemaker 10 has leads 14 that are used to connect the pacemaker 10 to the patient's heart 16. The pacemaker 10 applies pacing pulses to the heart 16 as needed to maintain the patient's heart rhythm. At appropriate intervals, the pacemaker 10 applies an impedance measurement signal to the patient 12 using a suitable lead configuration. The pacemaker 10 also monitors the resulting signal across the patient's body using a suitable lead configuration.

If desired, the impedance measurement signal may be applied using an electrode on one of the cardiac leads 14 and the case (the external housing of the pacemaker 10). Unipolar leads have a single electrode. Bipolar leads have tip and ring electrodes. If the leads 14 are bipolar leads, an impedance measurement current signal may be applied to the body 12 between a ring electrode and the case of the pacemaker 10. The resulting voltage signal can be measured between the tip electrode and the case of the pacemaker 10. When it is desired to measure the patient's external heartbeat signals, a conventional electrocardiogram machine 18 is connected to the patient 12 using electrodes 20.

Figure 2:
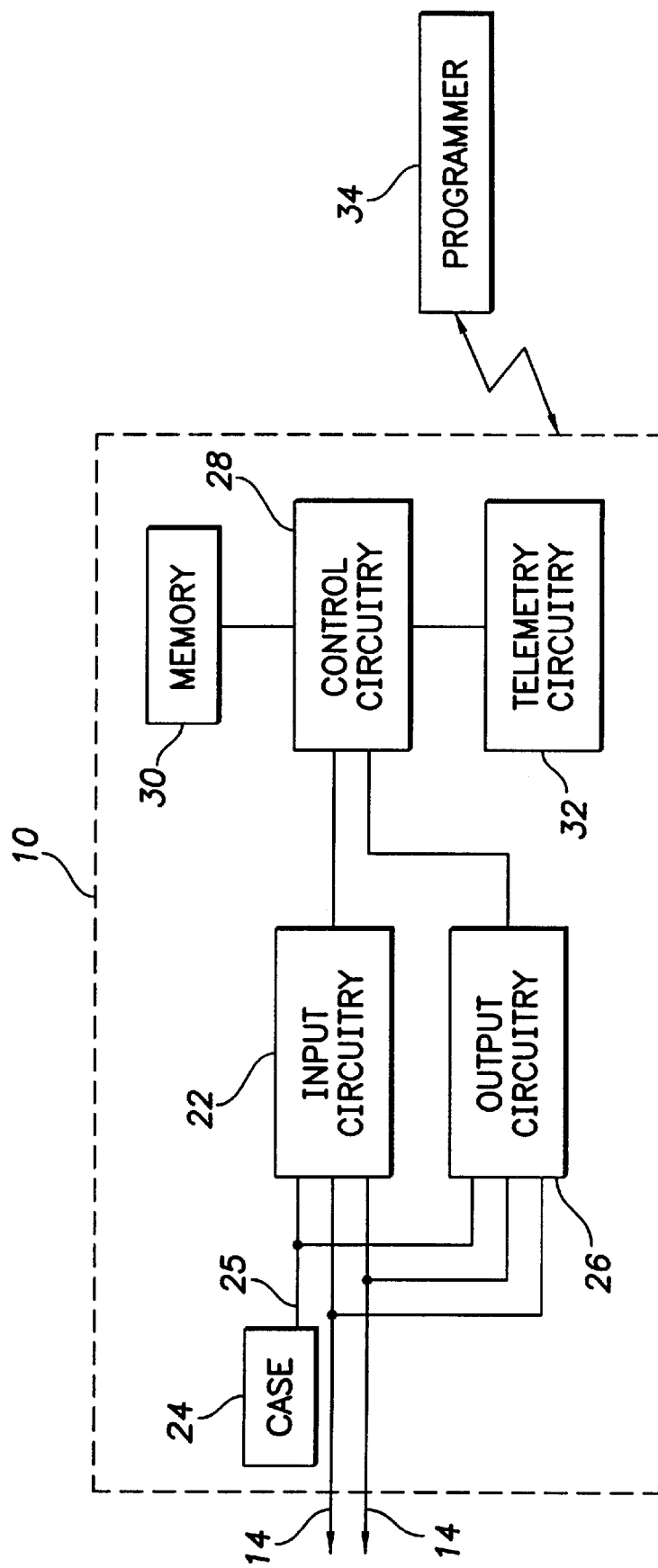
FIG. 2 is a schematic diagram illustrating a pacemaker configuration in accordance with the present invention.

The pacemaker 10 is shown in more detail in FIG. 2. Input circuitry 22 is connected to the case 24 and to the heart 16 via a line 25 and the leads 14, respectively. Output circuitry 26 is also connected to the case 24 and to the heart 16 via a line 25 and the leads 14, respectively. The input circuitry 22 and the output circuitry 26 are connected to control circuitry 28, which is preferably microprocessor-based. The control circuitry 28 controls the operation of the pacemaker 10 based on the execution of instructions stored in a memory 30. The pacemaker 10 may transmit data signals from within the patient 12 (FIG. 1) using telemetry circuitry 32. Data signals transmitted by the telemetry circuitry 32 are picked up by a conventional programmer 34. A physician can use the programmer 34 to adjust various programmable parameters of the pacemaker 10 by sending control signals to the pacemaker 10 via the telemetry circuitry 32.

The input circuitry 22 monitors the cardiac signals of the heart 16 to confirm the presence of cardiac events such as P-waves and R-waves. The control circuitry 28 analyzes the cardiac signals monitored by the input circuitry 22 and determines when the output circuitry 26 should apply pacing pulses to the heart 16.

To measure the impedance of the body for the purposes of determining the appropriate rate at which pacing pulses should be applied to the heart, the output circuitry 26 preferably generates an impedance measurement signal. The input circuitry 22 measures the resulting signal across the heart. The control circuitry 28 analyzes the impedance measurement signal generated by the output circuitry 26 and the resulting signal measured by the input circuitry 22 to determine the impedance of the body of the patient 12 (FIG. 1). Typically, the impedance measurement signal is a current of known magnitude and the resulting signal measured across the body is a voltage signal. Alternatively, the impedance measurement signal applied to the body may be a voltage of a known magnitude. If the voltage of the applied impedance measurement signal is known, the resulting magnitude of the current of the signal through the body can be measured to determine body impedance. Analyzing the impedance measurement signal and the resulting signal to determine the impedance of the patient's body typically involves processing these signals to determine their relative magnitudes. For example, in the absence of significant capacitive or inductive effects, the impedance of the patient's body may be calculated using Ohm's law (i.e., body impedance equals measured voltage divided by applied current).

Figure 3:
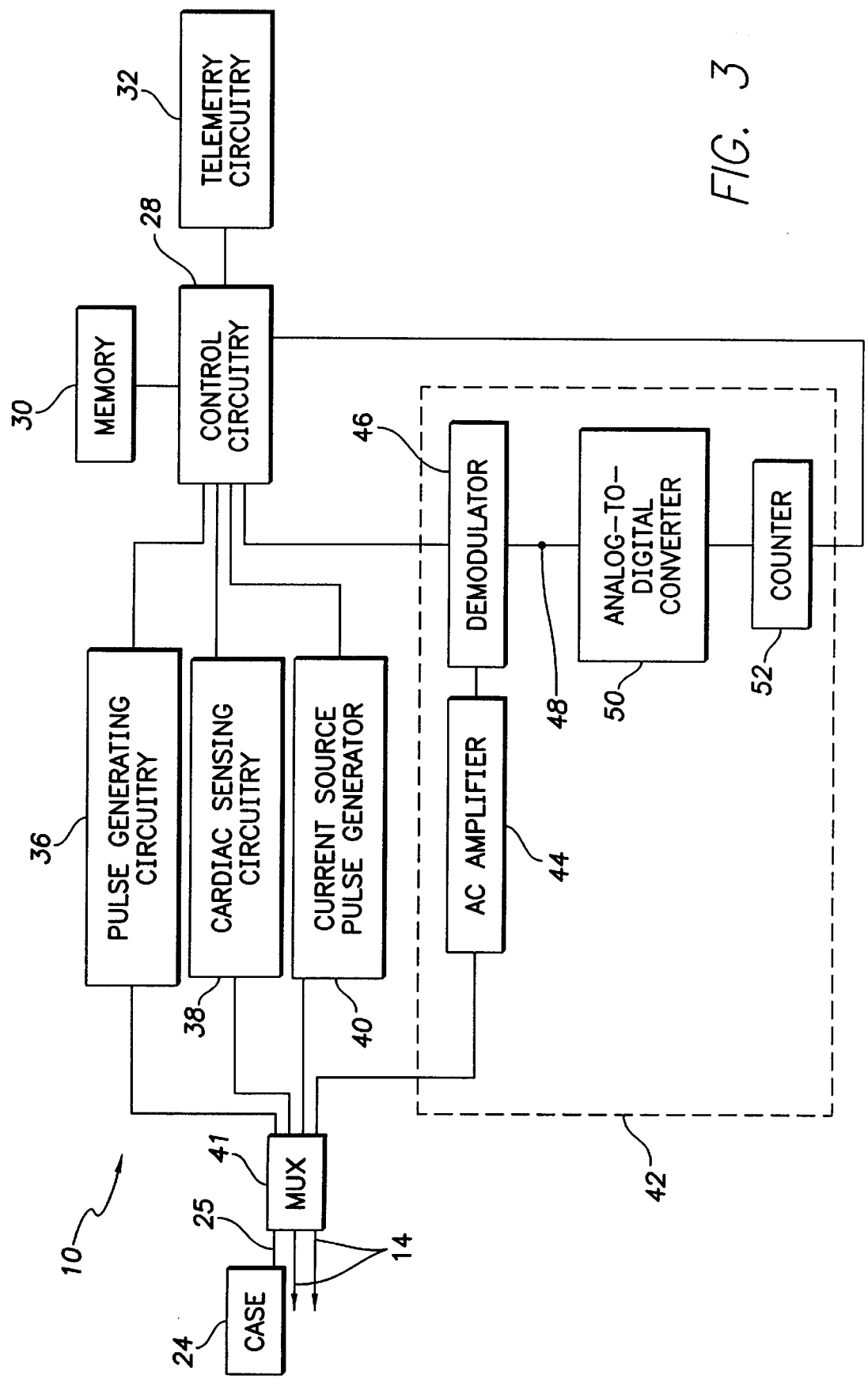
FIG. 3 is more detailed schematic diagram illustrating the pacemaker configuration of FIG. 2.

As shown in FIG. 3, the pacemaker 10 has pulse generating circuitry 36 for generating pacing pulses and cardiac sensing circuitry 38 for monitoring cardiac signals. The impedance measurement signal is preferably an AC (alternating current) impedance measurement current signal with a magnitude of 200 $\mu$A to 400 $\mu$A generated by a current source pulse generator 40. Applying the impedance measurement current signal across the body of the patient 12 (FIG. 1) gives rise to an impedance measurement voltage signal, which is measured using voltage signal measurement circuitry 42. The voltage signal measurement circuitry 42 preferably has an AC amplifier 44 for amplifying the measured voltage signal. A demodulator 46, which is similar to lock-in amplifier circuitry, rectifies the AC impedance measurement voltage signal and provides a DC (direct current) output voltage signal at an output terminal 48. The demodulator 46 is synchronized in time with the current source pulse generator 40 via control signals received from the control circuitry 28. The DC output voltage at the output 48 preferably ranges from 0 to 250 mV DC and is directly proportional to the impedance of the body of the patient 12 (FIG. 1).

The voltage at the output terminal 48 is digitized by an analog-to-digital converter 50, which is preferably of the type that is sensitive to changes in analog input voltage, such as a delta modulator. The analog input voltage received from the output terminal 48 is measured for a predetermined measurement period of 10 s to 20 s (preferably 15 s). During the predetermined period, a counter 52 is incremented by the analog-to-digital converter 50 in proportion to the magnitude and frequency of the analog input voltage. The output of the counter 52 is provided to the control circuitry 28, which analyzes the output of the counter 52 and the known magnitude of the impedance measurement signal generated by the current source pulse generator 40 to determine the impedance of the patient's body and adjust the pacing rate of the pacemaker 10 accordingly. The counter 52 is reset prior to initiating the next measurement period.

The impedance measurement signal used to determine the body impedance of the patient 12 (FIG. 1) is generated by the current source pulse generator 40. A multiplexer 41 is used to route signals between the leads 14 and the line 25 and the pulse generating and measurement circuitry of the pacemaker 10. For example, the multiplexer 41 connects the pulse generating circuitry 36 to the leads 14 and the line 25 when it is desired to provide a pacing pulse to the heart 16 (FIG. 1). During delivery of a pacing pulse, the multiplexer 41 disconnects the cardiac sensing circuitry 38, the current source pulse generator 40, and the voltage signal measurement circuitry 42 from the leads 14 and the line 25.

As long as the pulse generating circuitry 36 is not applying a pacing pulse to the heart 16 (FIG. 1), the multiplexer 41 connects the cardiac sensing circuitry 38 to the appropriate combination of the leads 14 and the line 25, so that cardiac signals can be monitored. The multiplexer 41 also connects the current source pulse generator 40 to the leads 14 and the line 25 in the desired configuration for applying the impedance measurement signal (e.g., connecting the current source pulse generator 40 to a ring electrode and the case 24). The multiplexer 41 also connects the voltage signal measurement circuitry 42 to the leads 14 and the line 25 as needed for measuring the resulting voltage signal across the patient's body (e.g., between a tip electrode and the case 24).

Conventional impedance measurement signals are made up of a series of square waves, which interfere with external monitoring equipment such at the ECG machine 18 (FIG. 1). In contrast, the current source pulse generator 40 (FIG. 3) generates measurement signals made up of a series of multiphasic waveforms that are not readily detected during measurements using the ECG machine 18.

Figure 4:
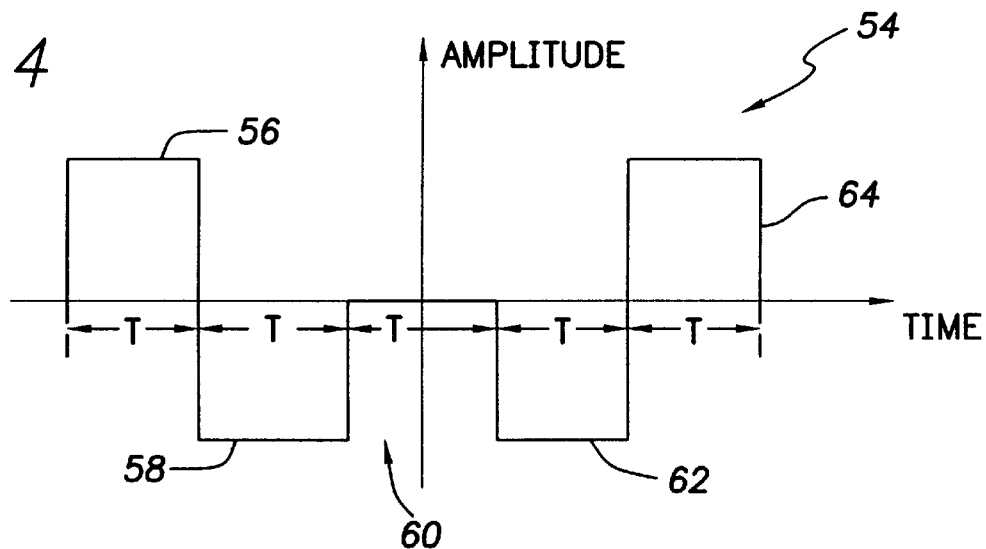
FIG. 4 is an illustrative pentaphasic impedance measurement waveform in accordance with the present invention.

An illustrative multiphasic waveform 54 is shown in FIG. 4. The first portion of waveform 54 contains a pulse 56 with a positive polarity and a pulse 58 with a negative polarity, each preferably of equal magnitude and of length T. A null period 60, also preferably of length T, follows the negative pulse 58. A negative pulse 62 and a positive pulse 64 follow the null period 60. Preferably, the negative pulse 62 and the positive pulse 64 are equal in magnitude to the pulse 56 and the pulse 58 and also are of length T. Suitable values for the length T are from 15 $\mu$s to 50 $\mu$s. Preferably, the length T is 30.5 $\mu$s, so that the waveform 54 has a total duration of 152.5 $\mu$s.

Figure 5:
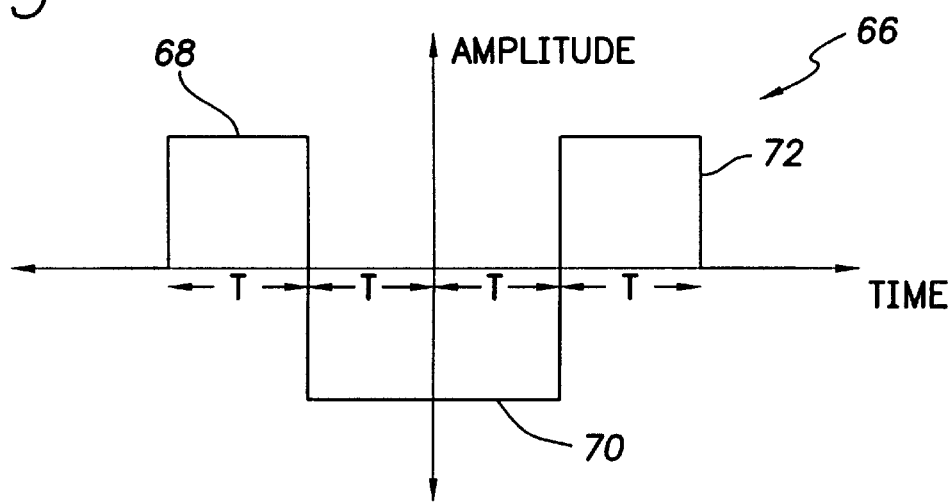
FIG. 5 is an illustrative triphasic impedance measurement waveform in accordance with the present invention.

Another waveform that may be generated by the current source pulse generator 40 is multiphasic waveform 66, shown in FIG. 5. The waveform 66 has a positive pulse 68 of length T. A negative pulse 70 of preferably the same magnitude as the pulse 68 and having a length of 2 T follows the positive pulse 68. A positive pulse 72 of the same magnitude and length as the positive pulse 68 follows the negative pulse 70.

Reversing the polarity of the individual pulses in the waveforms 54 (FIG. 4) and 66 (FIG. 5) does not affect the efficacy of the impedance measurement signal. If desired, negative pulses can be replaced with positive pulses and the positive pulses replaced by negative pulses. The multiphasic waveforms 54 (FIG. 4) and 66 (FIG. 5) do not interfere with the ECG machine 18 (FIG. 1) because the waveforms 54 (FIG. 4) and 66 (FIG. 5) have no DC component, meaning zero value after integration. Furthermore, it has zero value after second integration. Because of these characteristics, the impedance measurement signal of the present invention does not create significant interference in the approximately 1–240 Hz frequency range in which typical ECG machines are sensitive, so that interference with the ECG machine 18 (FIG. 1) is minimized. Similarly, the waveform 66 of FIG. 5 has a zero DC component and zero value after twice integration.

Figure 6A:
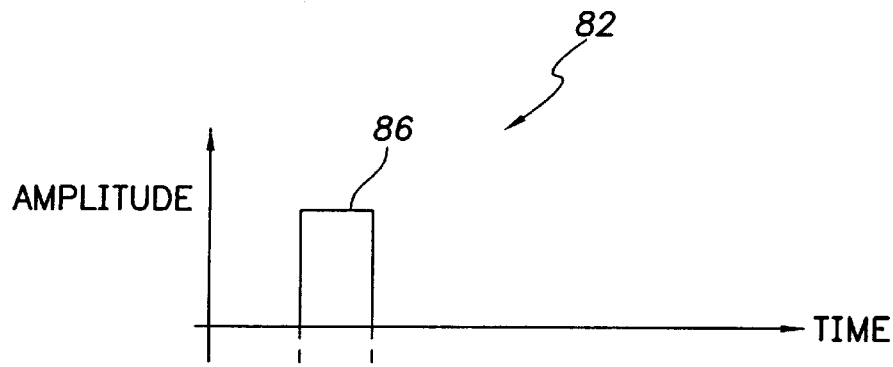
FIG. 6(a) is a graph of a conventional impedance measurement signal.
Figure 6B:
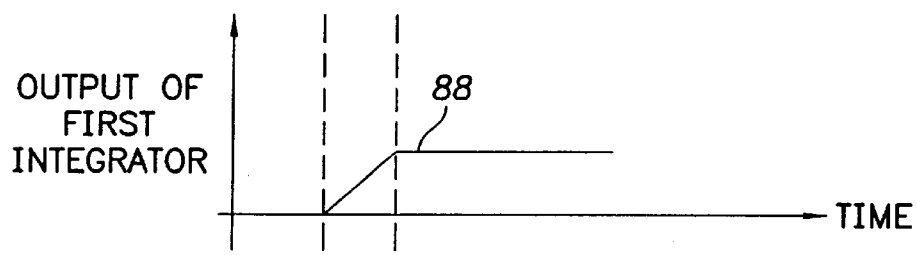
FIGS. 6(b) and (c) illustrate the behavior of a two-stage integrator when exposed to the conventional impedance measurement signal of FIG. 6(a)
Figure 6C:
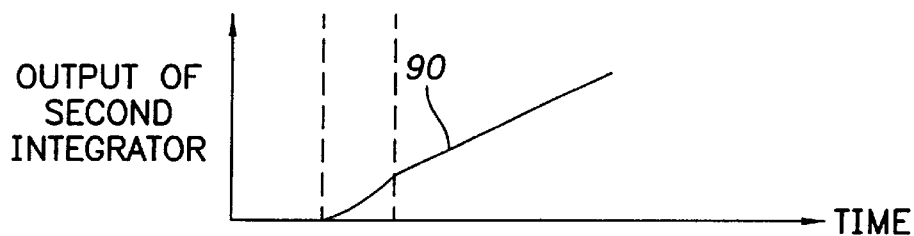
Figure 7A:
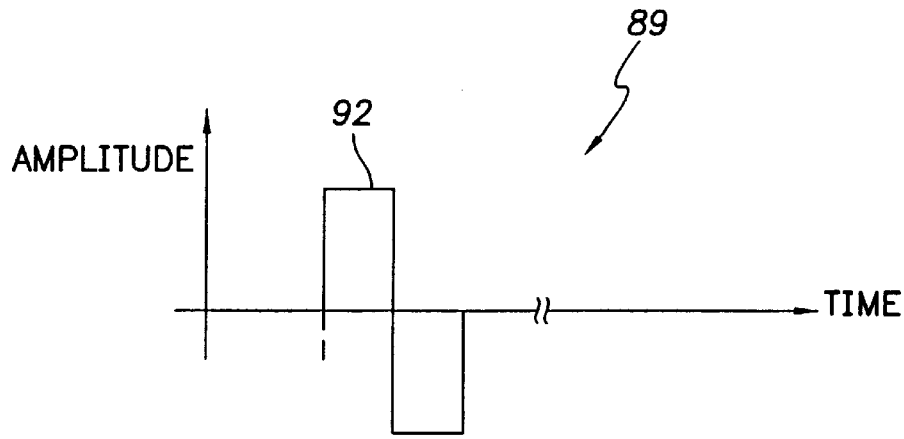
FIG. 7(a) is a graph of further conventional impedance measurement signal.

The way in which the multiphasic waveforms 54 (FIG. 4) and 66 (FIG. 5) reduce interference with ECG measurements taken by the ECG machine 18 (FIG. 1) is further illustrated in connection with FIGS. 6–8. Conventional impedance measurement signals 82 and 84 are shown in FIGS. 6($a$) and 7($a$), respectively. An impedance measurement signal 85 in accordance with the present invention and based on a multiphasic waveform 98 is shown in FIG. 8($a$).

A conventional ECG machine such as the ECG machine 18 of FIG. 1 can be modelled as an amplifier containing an integrator of second order or higher, creating a second order low pass filter portion of their band pass filter. The nature of the response of such an amplifier to the signals of FIGS. 6($a$), 7($a$), and 8($a$) is illustrated in parts ($b$) and ($c$) of FIGS. 6–8. FIGS. 6($b$), 7($b$), and 8($b$) illustrate the response of a first order integrator to the signals of FIGS. 6($a$), 7($a$), and 8($a$), respectively. FIGS. 6($c$), 7($c$), and 8($c$) illustrate the response of a second order integrator to the signals of FIGS. 6($a$), 7($a$), and 8($a$), respectively.

The magnitude of the output of the second integrator shown in FIGS. 6($c$), 7($c$), and 8($c$) is representative of the sum-total harmonic content of all of the signals that pass though the second order integrator that is being used to model the ECG machine 18 (FIG. 1). The integrator outputs shown in FIGS. 6–8 are not mathematically rigorous, but are satisfactory for the purpose of comparing the magnitude of the response of the ECG machine 18 (FIG. 1) to the impedance measurement signals 82, 84, and 85 of FIGS. 6($a$), 7($a$), and 8($a$).

The impedance measurement signal 82 of FIG. 6($a$) is one that has been used in conventional pacemakers. The impedance measurement signal 82 is made up of 15 $\mu$s positive pulses 86 spaced at 50 ms intervals (a repetition rate of 20 Hz). A first order integrator exhibits a corresponding response 88 to the signal 82, as shown in FIG. 6($b$). A second order integrator exhibits a response 90 to the impedance measurement signal 82, as shown in FIG. 6($c$). The way in which the response 90 increases as a function of time indicates that the ECG machine 18 (FIG. 1) is sensitive to impedance measurement signals with the characteristics shown in FIG. 6($a$) and is therefore prone to interference from the impedance measurement signal 82.

Figure 7B:
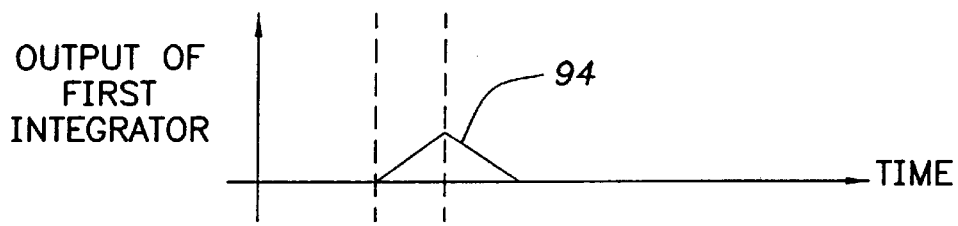
FIGS. 7(b) and (c) illustrate the behavior of a two-stage integrator when exposed to the conventional impedance measurement signal of FIG. 7(a)
Figure 7C:
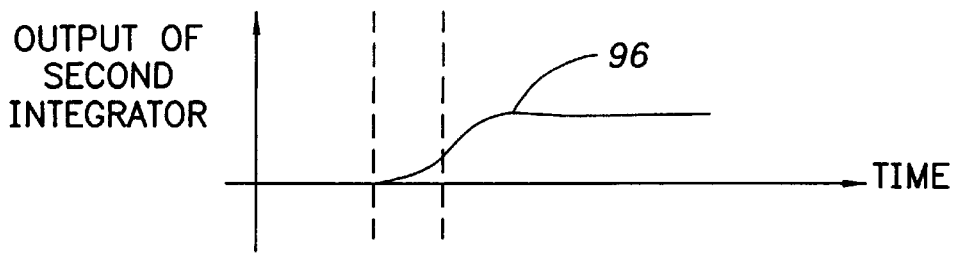

The impedance measurement signal 84 of FIG. 7($a$) has also been used in conventional pacemakers. The impedance measurement signal 84 is made up of 15 $\mu$s alternating positive and negative pulses 92 spaced at 62.5 ms intervals (a repetition rate of 16 Hz). A first order integrator exhibits a corresponding response 94 to the signal 84, as shown in FIG. 7($b$). A second order integrator exhibits a response 96 to the impedance measurement signal 84, as shown in FIG. 7($c$). The first order response 94 has a smaller magnitude than the first order response 88 of FIG. 6($b$), which indicates that the impedance measurement signal 84 of FIG. 7($a$) will be amplified less by the ECG machine 18 (FIG. 1) than the impedance measurement signal 82 of FIG. 6($a$). The conventional 15 microsecond pulses are too short to accommodate larger feedthrough capacitors. Larger feedthrough capacitors are required to avoid interference from cellular telephones.

An impedance measurement signal 85 in accordance with the present invention is shown in FIG. 8($a$). The impedance measurement signal 85 is made up of a series of multiphasic waveforms 98, each having positive pulse 100 and 102, negative pulses 104 and 106, and a null period 108. The length of each of the pulses 100, 102, 104 and 106 and the null period 108 is preferably 30.5 $\mu$s. The pulses 100, 102, 104, and 106 are preferably of equal magnitude. The pentaphasic pulse sequence is one example of a wave form, which, after passing through the feedthrough capacitors, provides two equal peak-to-peak resultant voltage measurements to be averaged together. Feedthrough capacitors are used for EMI protection in pacemakers.

A first order integrator exhibits a response 110 to the impedance measurement signal 85, as shown in FIG. 8($b$). A second order integrator exhibits a response 112 to the impedance measurement signal 85, as shown in FIG. 7($c$). The first order response 110 has a smaller magnitude than the responses 88 of FIG. 6($b$) and 94 of FIG. 7($b$), which indicates that the ECG machine 18 (FIG. 1) is less sensitive to signals with the characteristics of the impedance measurement signal 85 than to conventional impedance measurement signals 82 of FIG. 6($a$) and 84 of FIG. 7($a$). In addition, the second order response 112 is smaller than the response 90 of FIG. 6($c$) and the response 90 of FIG. 7($c$), which further indicates that the ECG machine 18 (FIG. 1) is less sensitive to signals with the characteristics of the impedance measurement signal 85 than to the conventional impedance measurement signals 82 of FIG. 6($a$) and 84 of FIG. 7($a$).

Figure 8A:
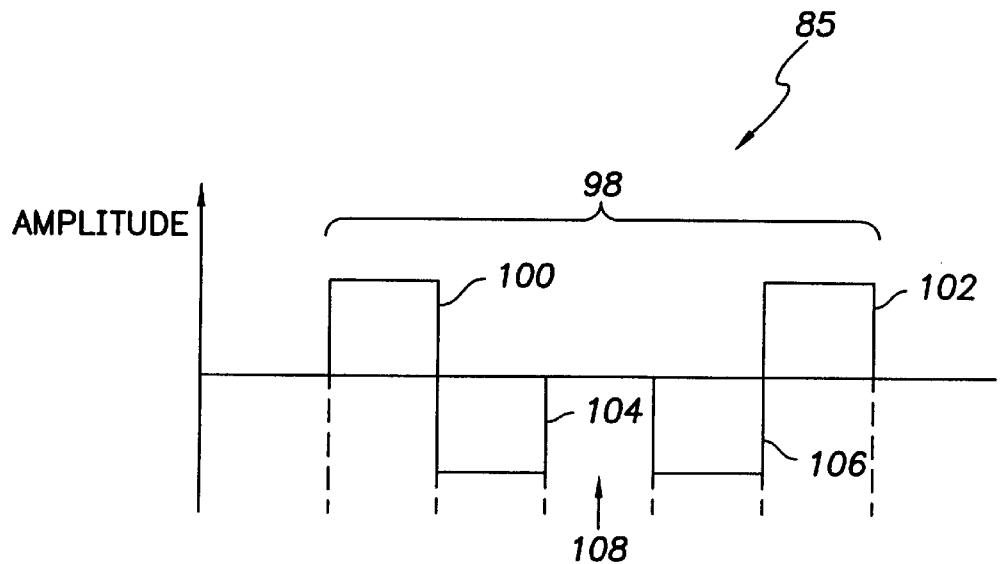
FIG. 8(a) is a graph of an illustrative impedance measurement signal in accordance with the present invention.
Figure 8B:
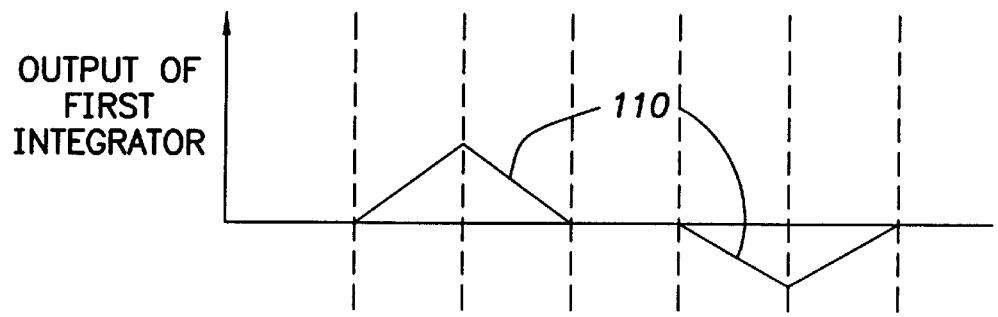
FIGS. 8(b) and (c) illustrate the behavior of a two-stage integrator when exposed to the impedance measurement signal of FIG. 8(a).
Figure 8C:
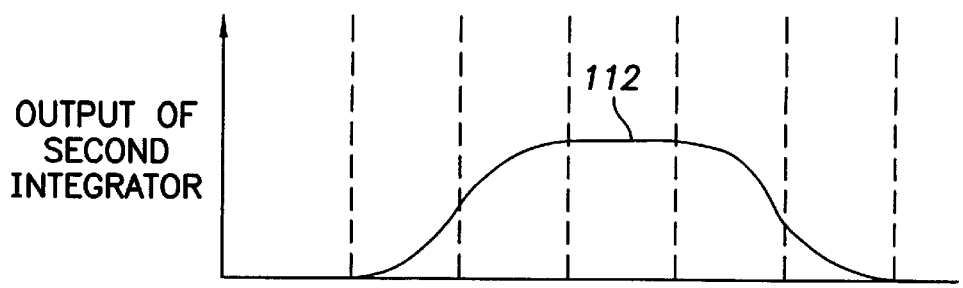

The modelling results of FIGS. 6–8 have also been confirmed by measuring the spectral content of the signals 82, 84, and 85 of FIGS. 6(a), 7(a), 8(a) using a spectrum analyzer. Direct measurements of this type have shown that in the frequency range of typical ECG machines (1–240 Hz), the magnitudes of the signal components of the impedance measurement signal 85 of FIG. 8(a) are significantly lower than those for signals 82 of FIG. 6(a) and 84 of FIG. 7(a).

Thus methods and apparatus for measuring the body impedance of a patient have been provided for use in a rate-responsive pacemaker. Impedance measurements are made to determine the rate at which to pace a patient's heart. Control circuitry is provided that directs the operation of the pacemaker. Input circuitry connected to the control circuitry monitors the patient's heartbeat signals. Output circuitry is used to provide pacing pulses to the heart.

The output circuitry is also used to generate an impedance measurement signal that is applied to the patient's body. The impedance measurement signal may be a current signal made up of a series of multiphasic impedance measurement waveforms. The waveforms have a zero DC component and have zero value after second integration.

One skilled in the art will appreciate that the present invention can be practiced by other than the described embodiments, which are presented for the purposes of illustration and not of limitation, and the present invention is limited only by the claims that follow.

What is claimed is:

1. Apparatus implantable in a patient's body for determining the impedance of the patient's body, the apparatus being compatible with external devices which detect a desired body signal, the external device having second order low pass filtering characteristics corresponding to a second order integration of the desired body signal, comprising:

impedance signal generating means for generating an impedance measurement signal having a series of substantially equally spaced multiphasic impedance measurement waveforms, each multiphasic impedance measurement waveform having a zero DC component and zero average after a first order integration by the external device, whereby the multiphasic waveform results in a zero value after the second order integration by the external device;

means for applying the impedance measurement signal to the body and thus producing a resulting signal across the body;

means for measuring the resulting signal; and means for determining the impedance of the body by analyzing the resulting signal.

2. The apparatus of claim 1, wherein the means for measuring the resulting signal further comprises voltage measurement circuitry.

3. The apparatus of claim 2, wherein the voltage measurement circuitry comprises:

an AC amplifier for amplifying the resulting signal;

a demodulator for rectifying the resulting signal after the resulting signal is amplified by the AC amplifier; and an analog-to-digital converter for digitizing the resulting signal after the resulting signal is rectified by the demodulator.

4. The apparatus of claim 1, wherein the impedance signal generating means further comprises waveform generating means for generating a series of equally spaced pentaphasic impedance measurement waveforms, each pentaphasic impedance measurement waveform comprising:

a first pulse of a predetermined magnitude and a predetermined length;

a second pulse immediately following the first pulse, the second pulse being of opposite polarity to the first pulse and having the predetermined magnitude and the predetermined length;

a null period of the predetermined length following the second pulse;

a third pulse immediately following the null period, the third pulse being of opposite polarity to the first pulse and having the predetermined magnitude and the predetermined length; and a fourth pulse immediately following the third pulse, the fourth pulse being of opposite polarity to the third pulse and having the predetermined magnitude and the predetermined length.

5. The apparatus of claim 1, wherein the impedance signal generating means further comprises waveform generating means for generating a series of equally spaced triphasic impedance measurement waveforms, each triphasic impedance measurement waveform comprising:

a first pulse of a predetermined magnitude and a predetermined length;

a second pulse immediately following the first pulse, the second pulse being of opposite polarity to the first pulse and having the predetermined magnitude and a length of twice the predetermined length; and a third pulse immediately following the second pulse, the third pulse being of opposite polarity to the second pulse and having the predetermined magnitude and the predetermined length.

6. The apparatus of claim 1, wherein the impedance signal generating means further comprises a current source pulse generator.

7. The apparatus of claim 1, wherein the impedance signal generating means further comprises means for providing the multiphasic waveforms with durations in a range of approximately 45 $\mu$s to 250 $\mu$s.

8. The apparatus of claim 1, further comprising:

means for determining the patient's respiration rate based on the measured impedance, the patient's respiration rate being indicative of metabolic need;

means for determining a pacing rate at which to apply pacing pulses to the heart of the patient based on the patient's respiration rate; and means for applying the pacing pulses to the heart at the pacing rate;

whereby the apparatus is a rate-responsive pacemaker.

9. The apparatus of claim 1, wherein the means for determining the impedance further comprises means for analyzing the magnitudes of the resulting signal and the impedance measurement signal.

10. A rate-responsive pacemaker for measuring the impedance of a patient's body and applying pacing pulses to the heart of the patient at a rate based on the impedance, the pacemaker being compatible with external devices which detect a desired body signal, the external device having second order low pass filtering characteristics corresponding to a second order integration of the patient's cardiac signal, comprising:

impedance signal generating means for generating an impedance measurement signal having a series of equally spaced multiphasic impedance measurement waveforms, each multiphasic impedance measurement waveform having a zero DC component and zero value after the second integration by the external device;

means for applying the impedance measurement signal to the body and thus producing a resulting signal across the body;

means for measuring the resulting signal;

means for determining the impedance of the body by analyzing the resulting signal;

means for determining the rate at which to apply pacing pulses to the heart based on the impedance; and means for applying the pacing pulses to the heart at the rate.

11. The pacemaker of claim 10, wherein the means for measuring the resulting signal further comprises voltage measurement circuitry.

12. The pacemaker of claim 11, wherein the voltage measurement circuitry comprises:

an AC amplifier for amplifying the resulting signal;

a demodulator for rectifying the resulting signal after the resulting signal is amplified by the AC amplifier; and an analog-to-digital converter for digitizing the resulting signal.

13. The pacemaker of claim 10, wherein the impedance signal generating means further comprises waveform means for generating a series of equally spaced pentaphasic impedance measurement waveforms, each pentaphasic impedance measurement waveform comprising:

a first pulse of a predetermined magnitude and a predetermined length;

a second pulse immediately following the first pulse, the second pulse being of opposite polarity to the first pulse and having the predetermined magnitude and the predetermined length;

a null period of the predetermined length following the second pulse;

a third pulse immediately following the null period, the third pulse being of opposite polarity to the first pulse and having the predetermined magnitude and the predetermined length; and a fourth pulse immediately following the third pulse, the fourth pulse being of opposite polarity to the third pulse and having the predetermined magnitude and the predetermined length.

14. The pacemaker of claim 10, wherein the impedance signal generating means further comprises waveform means for generating a series of equally spaced triphasic impedance measurement waveforms, each triphasic impedance measurement waveform comprising:

a first pulse of a predetermined magnitude and a predetermined length;

a second pulse immediately following the first pulse, the second pulse being of opposite polarity to the first pulse and having the predetermined magnitude and a length of twice the predetermined length; and a third pulse immediately following the second pulse, the third pulse being of opposite polarity to the second pulse and having the predetermined magnitude and the predetermined length.

15. The pacemaker of claim 10, wherein the impedance signal generating means further comprises a current source pulse generator.

16. The pacemaker of claim 10, wherein the impedance signal generating means further comprises means for providing the multiphasic waveforms with durations in a range of approximately 45 $\mu$s to 250 $\mu$s.

17. The pacemaker of claim 10, wherein the means for determining the impedance further comprises means for analyzing the magnitudes of the resulting signal and the impedance measurement signal.

18. A rate-responsive implantable stimulation device, the device being compatible with external devices which monitor the patient's cardiac signal and have second order low pass filtering characteristic corresponding to a second order integration of the cardiac signal, the stimulation device comprising:

first pulse generating means for generating a multiphasic waveform to the heart, the multiphasic waveform having a series of pulses with a predefined sequence of polarities such that the multiphasic waveform has a zero value after the second order integration by the external device;

measuring means for measuring a resulting signal in response to the multiphasic waveform;

processing means, coupled to the measuring means, for determining the impedance of the body by analyzing the resulting signal, for determining the patient's respiration rate based on the measured impedance, and for determining a stimulation rate based on the patient's respiration rate; and second pulse generating means, triggered by the processing means, for generating stimulation pulses at the stimulation rate.

19. The stimulation device of claim 18, wherein:

the device includes a feedthrough capacitor for EMI protection; and the series of pulses with the predefined sequence of polarities, after passing through the feedthrough capacitor, comprises two equal peak-to-peak resultant voltage measurements that when integrated by the second order filter produces a zero value.

20. The stimulation device of claim 19, wherein:

the multiphasic waveform comprises a pentaphasic pulse sequence.

21. The stimulation device of claim 19, wherein:

the multiphasic waveform comprises a triphasic pulse sequence.

22. The stimulation device of claim 18, wherein:

the multiphasic waveform further has a zero value after the first order integration by the external device;

whereby the stimulation device is compatible with external devices having first order low pass filter characteristics.

* * * * *